United States Patent
Schurr

(10) Patent No.: US 7,513,914 B2
(45) Date of Patent: Apr. 7, 2009

(54) MEDICAL IMPLANT

(76) Inventor: Marc O. Schurr, Schwabstrasse 15, Tubingen 72074 (DE)

(*) Notice: Subject to any disclaimer, the term of this patent is extended or adjusted under 35 U.S.C. 154(b) by 0 days.

(21) Appl. No.: 10/722,109

(22) Filed: Nov. 25, 2003

(65) Prior Publication Data

US 2004/0138760 A1    Jul. 15, 2004

Related U.S. Application Data

(63) Continuation-in-part of application No. PCT/EP02/05810, filed on May 27, 2002.

(30) Foreign Application Priority Data

May 27, 2001  (DE) ............................... 101 25 568
Nov. 30, 2001  (DE) ............................... 101 58 785

(51) Int. Cl.
*A61F 2/04* (2006.01)
(52) U.S. Cl. .................................. 623/23.65; 604/8
(58) Field of Classification Search ................. 623/1.13, 623/1.36, 11.11, 14.13, 23.64, 23.65, 23.67, 623/1.3; 604/8, 9; 606/153
See application file for complete search history.

(56) References Cited

U.S. PATENT DOCUMENTS

| | | | |
|---|---|---|---|
| 4,315,509 A | 2/1982 | Smit | 128/303 |
| 4,416,267 A | 11/1983 | Garren et al. | 128/1 |
| 5,246,456 A * | 9/1993 | Wilkinson | 623/23.65 |
| 5,306,300 A | 4/1994 | Berry | 623/11 |
| 5,820,584 A * | 10/1998 | Crabb | 604/500 |
| 5,861,036 A | 1/1999 | Godin | 623/12 |
| 6,146,414 A | 11/2000 | Gelman | 623/1 |
| 2002/0022891 A1 * | 2/2002 | Chevillon et al. | 623/23.64 |
| 2004/0039452 A1 * | 2/2004 | Bessler | 623/23.65 |

FOREIGN PATENT DOCUMENTS

WO    WO 88/05671    8/1988

OTHER PUBLICATIONS

Lambert et al., Intestinal absorption of vitamin B12 in rats with gastric resection or gastric diversion., Comptes Rendus des Seances de la Societe de Biologie et de Ses Filiales (1965), 159(11), 2212-17. English Abstract provided.*
International Search Report dated Sep. 4, 2002.

* cited by examiner

*Primary Examiner*—William H. Matthews
(74) *Attorney, Agent, or Firm*—Bromberg & Sunstein LLP

(57) ABSTRACT

A medical implant is disclosed, said implant having a flexible hollow body (1) which can be implanted inside the stomach (8) of a patient and which has a first tube-like end section (2) and a second tube-like end section (3), wherein the first tube-like end section (2) is dimensioned such that it can be fitted into the esophagus (7) of the patient, and the second tube-like end section (3) is dimensioned such that it can be connected to the small intestine loop (9) of the patent in a sealing manner.

6 Claims, 3 Drawing Sheets

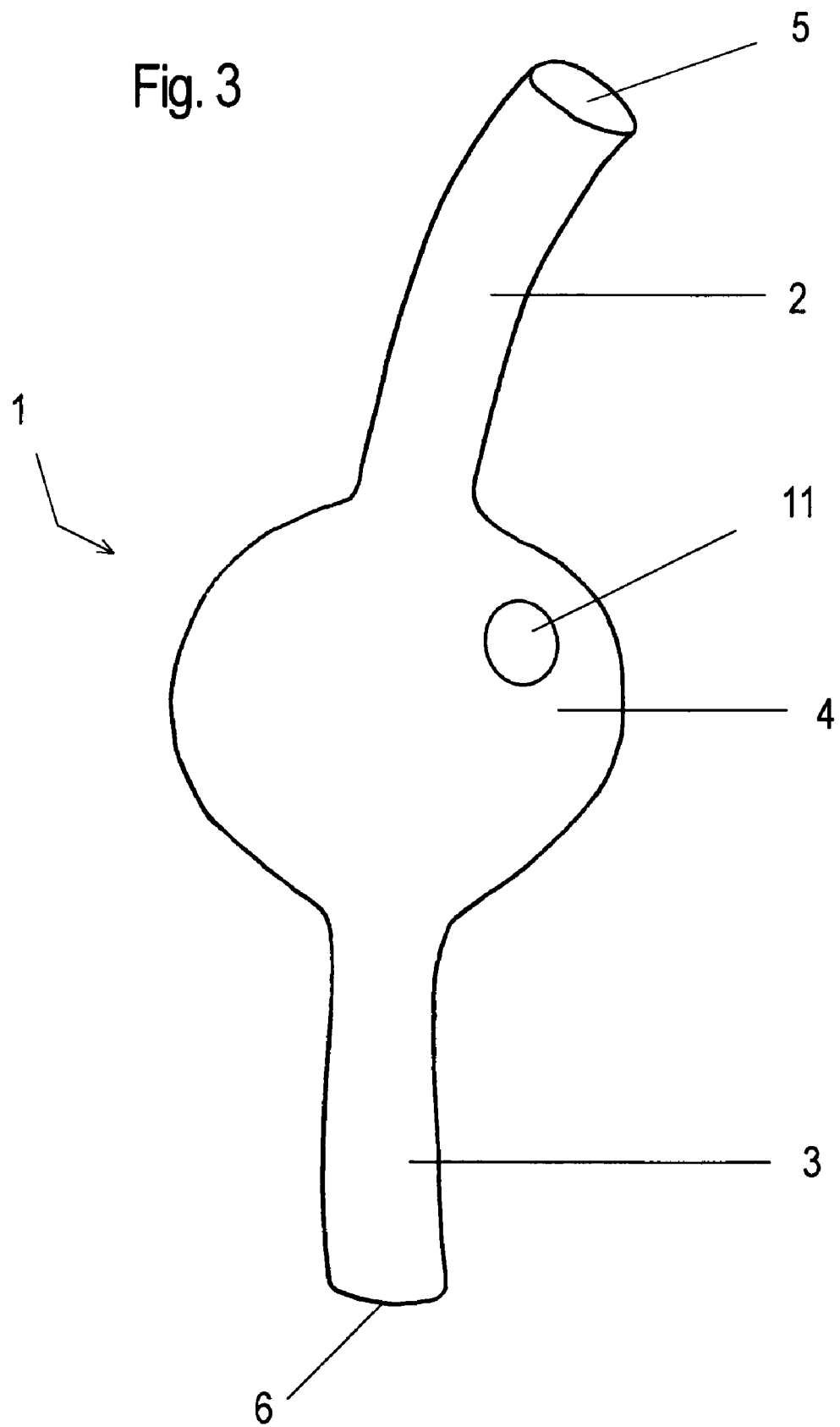

ID IMPLANT

The present application is a continuation-in-part of PCT application no. PCT/EP02/05810, filed May 27, 2002, which claims priority from German application no. 101 25 568.3, filed May 27, 2001, and from German application no. 101 58 785.6, filed Nov. 30, 2001. All of these applications are incorporated herein by reference.

FIELD OF THE INVENTION

The present invention relates to a device for treating pathological obesity and especially to a medical implant which is adapted to bypass a natural food passage in the digestive tract.

BACKGROUND OF THE INVENTION

The so-called Body Mass Index (BMI), is used today to define the degree to which one is overweight. BMI is calculated by dividing body weight in kilograms (kg) by the square of the body height in meters (m$^2$). A BMI of more than 40 corresponds to morbid obesity. A BMI of 35-40 is defined as severe obesity and a BMI of 30-35 is defined as obese. Morbid obesity and, to a lesser extent, severe obesity of human beings results in a number of health consequences such as cardiovascular diseases, diabetes and damages of the locomotor system.

As a general rule, in the case of extreme forms of obesity, often only a few kilograms of weight reduction, which is hardly noticeable, is achieved over the long run despite all efforts. In such extreme cases, surgical therapy is often finally indicated.

Nowadays, surgical therapies for the morbidly obese include performing operations for restricting the stomach. Among these, "gastric banding" and the "gastric bypass", in which appropriate implants are inserted, have been generally accepted.

Gastric Banding

With this operation the inlet area of the stomach is constricted by an implanted synthetic band, thereby forming a smaller upper stomach sac which communicates with the remaining stomach area only through a small outlet.

However, this operation can result in the patient eating more high-caloric food after the operation or the constricted stomach bag bulges and expands so that a certain increase in weight is probable again. Moreover, it is possible for the silicone band to be displaced or break through into the stomach.

Gastric Bypass

By this operation a smaller stomach bag in the inlet area of the stomach is likewise separated from the main portion of the stomach, defined with the aid of clip suture instruments. However, this stomach bag does not communicate with the remaining stomach area, but with an anastomosed loop of the small intestine which is pulled up and fixed to the stomach bag. The food passes through the esophagus and the smaller stomach bag and then flows into the loop of the small intestine, bypassing the remaining larger portion of stomach and much or all of the duodenum. Gastric bypass generally results in a higher reduction of weight than the gastric banding.

However, the operation is deemed to be irreversible, which is a drawback in the case of complications such as malabsorption consequences. Furthermore there is a risk that sutures at the clip suture instruments become leaky, thereby necessitating a further surgical procedure.

SUMMARY OF EXEMPLARY EMBODIMENTS OF THE INVENTION

It is the object of the invention to provide a device for treating pathological obesity which controls the obesity for a long time and permits a reversible operation on the patients.

The object is achieved by the device according to claim 1. Advantageous further developments are explained in the dependent claims.

The device is a medical implant comprising a storage-like hollow body which can be implanted inside the stomach of a patient as a kind of stomach mock-up for a temporary intake of food having a first tube-like end section and a second tube-like end section, the first tube-like end section being dimensioned so that it can be fitted into the esophagus of the patient and the second tube-like end section being dimensioned so that it can be connected to the loop of the small intestine of the patient in a sealing manner.

According to an advantageous further development a wall of the hollow body has a means for adjusting the volume of the hollow body.

In accordance with a further advantageous development the implant has fixing means at the first and second tube-like end sections for fixing the end sections to parts of the patient's organs. For instance, the fixing means can be braces, or the end sections can be easily sewed at the corresponding parts of the patient's organs.

According to a further advantageous development the implant includes between the first and second end sections a hollow flexible central portion which bulges relative to the end sections and is communicated with the latter.

Preferably, the central portion is made of a suitable flexible material such as polyurethane or another synthetic resin having a similar flexibility. The wall thickness of the central portion can be further adjusted to obtain the desired flexibility of the central portion. Advantageously, the desired flexibility of the central portion corresponds to the flexibility of a human stomach.

Optionally, a wall of the hollow body and especially of the central portion may include a means by which the diameter and thus the maximum volume of the hollow body is adjusted. For instance, the means for adjusting the diameter of the hollow body can be realized by inelastic strips enlacing the hollow body or being embedded therein. Alternatively, the central portion may be in the form of bellows.

The flexible hollow body can comprise an additional aperture directed to the stomach. The aperture is adjusted in its size and allows a natural passage for the food into the stomach. Thereby, the stomach is advantageously bypassed, for instance, for 90%, while 10% of the food comes into contact with the remaining stomach and the duodenum. Furthermore it is possible to observe the remaining stomach through the aperture, for instance, via an endoscope after surgery, which has been impossible in conventional and laparoscopic methods yet.

The aperture can include means for changing its size, such as a lace for contracting the aperture.

BRIEF DESCRIPTION OF THE DRAWINGS

The invention and its advantages become clear from the following description of the embodiment along with the enclosed drawings.

FIG. 3 shows a modified embodiment according to the present invention.

DETAILED DESCRIPTION OF EXEMPLARY EMBODIMENTS

Figure 1:
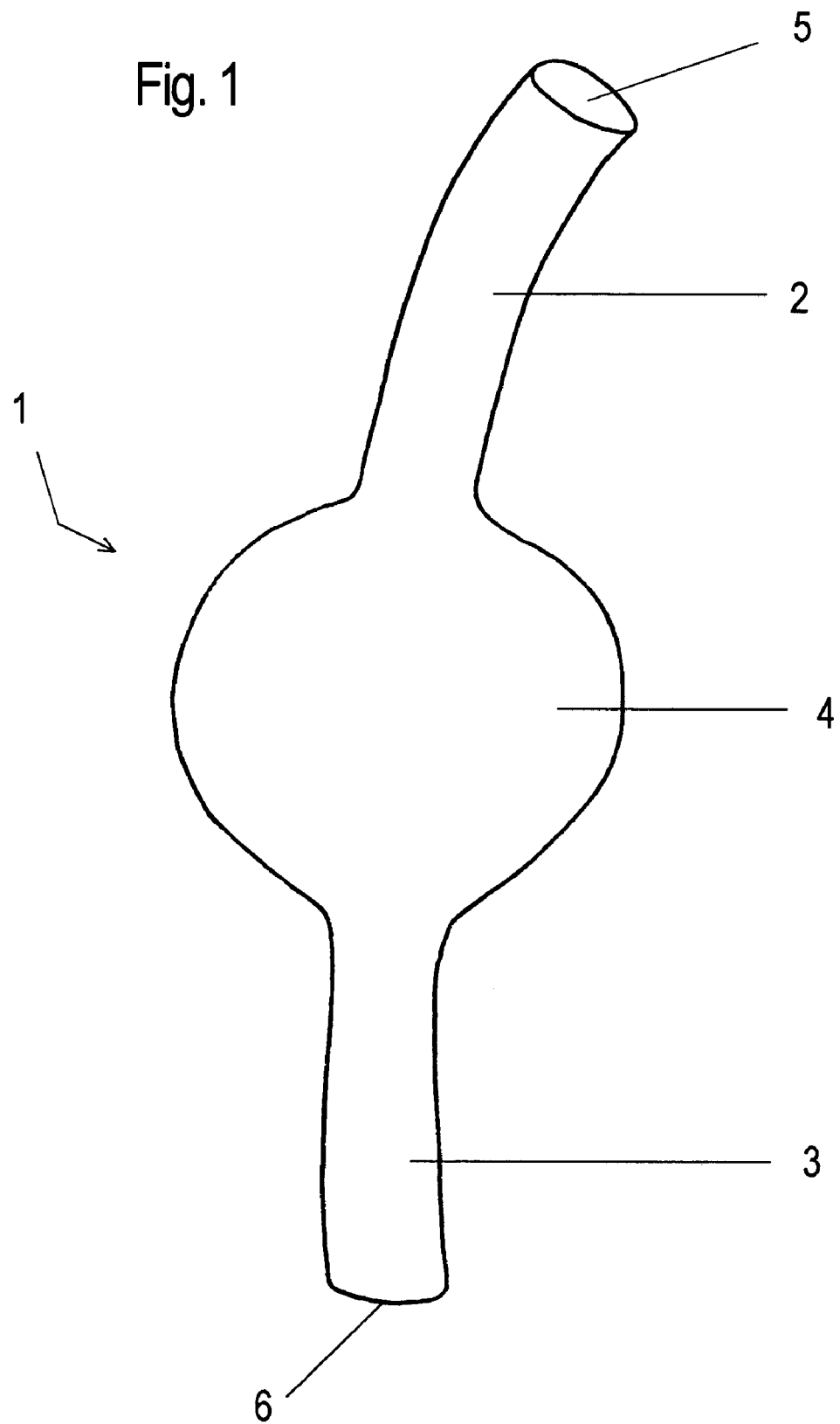
FIG. 1 shows an embodiment of the present invention.

FIG. 1 illustrates a medical implant for treating pathological obesity in accordance with the present invention. This implant is a flexible hollow body 1.

The hollow body 1 has a first tube-like end section 2 and a second tube-like end section 3. The first tube-like end section 2 is dimensioned so that it can be fitted into the esophagus of the patient. The second tube-like end section 3 is dimensioned so that it can be fitted into the loop of the small intestine of the patient.

Each of the first and second tube-like end sections 2, 3 includes a first opening 5 and a second opening 6, respectively.

Fixing means (not shown) by which the end sections 2, 3 can be fixed to parts of the patient's organs are provided at the first and second tube-like end sections 2, 3. The fixing means can be, for instance, braces which are broadly used in the medical area.

Alternatively, the end sections 2, 3 can be easily sewed at the corresponding parts of the patient's organs.

The hollow body 1 has a hollow flexible central portion 4 which is bulged relative to the first and second end sections 2, 3 and is communicated with the first and second end sections 2, 3. This central portion 4 defines the later artificial stomach volume of the patient. As the central portion 4 is flexible, the artificial stomach volume is expandable to a certain extent depending on the filling ratio of the central portion 4. Preferably, the central portion 4 is made of a suitable flexible material such as polyurethane or another synthetic resin having a similar flexibility. The wall thickness of the central portion 4 can be adjusted to obtain the desired flexibility of the central portion 4. Advantageously, the desired flexibility of the central portion 4 corresponds to the flexibility of a human stomach.

A wall of the hollow body 1 and especially of the central portion 4 may optionally include a means (not shown) by which the diameter and thus the maximum volume of the hollow body 1 is adjusted. For instance, the means for adjusting the diameter of the hollow body 1 can be realized by inelastic strips enlacing the hollow body 1 or being embedded therein. Alternatively, the central portion 4 may be in the form of bellows.

It is also possible, of course, to design the central portion as a rigid receptacle.

Figure 2:
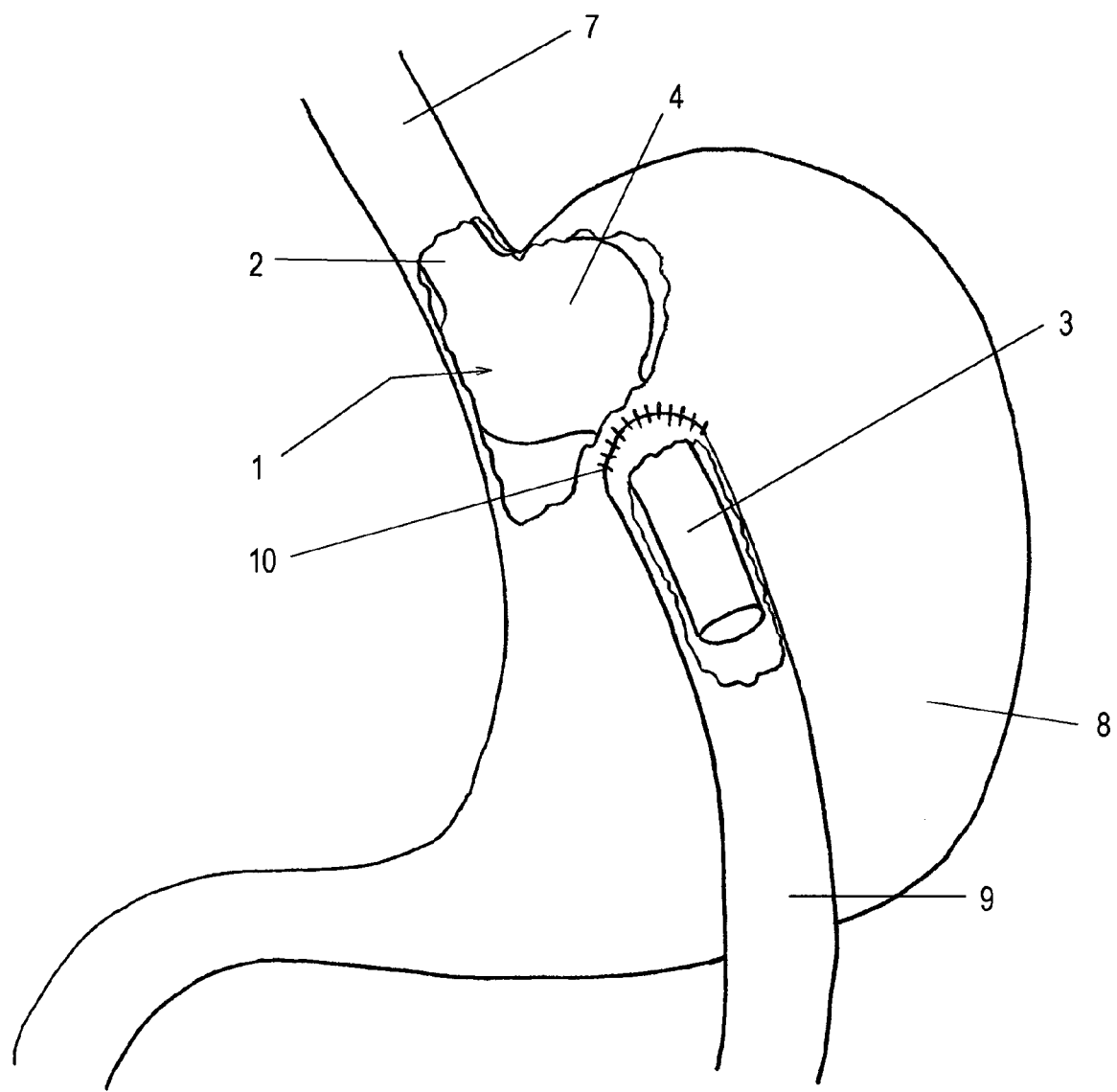
FIG. 2 shows the embodiment of the present invention while being implanted in the stomach of a patient.

FIG. 2 illustrates how the medical implant is used for treating pathological obesity according to an embodiment of the present invention by implantation in the stomach.

Here the arrangement of the implant in the stomach is clearly discernible. The first tube-like end section 2 is fitted into the esophagus 7, while the second tube-like end section 3 is fitted into a laxative loop of the small intestine 9. The small intestine loop 9 is prepared in advance by being circularly clipped to the stomach wall by clip suture instruments 10, after a suitable perforation in the stomach wall was prepared at that location. In this way the implant comprises a bypass between the esophagus 7 and the small intestine 9 which completely bypasses the stomach 8 and the duodenum (not shown). Thus the food path becomes the esophagus 7, through the first opening 5, the first tube-like end section 2, the central portion 4, the second tube-like end-section 3 and the second opening 6 directly into the small intestine. There is preferably chosen a laxative loop of the small intestine 9 from the lower small intestine area so that the upper area of the small intestine is equally bypassed.

The implant in accordance with the present invention has the following advantages.

The entire operation can be executed by minimally invasive surgery methods, whereby the stresses and risks for the patient are minimized.

In general the implant can be removed from the patient again, whereby the operation is reversible in contrast to the gastric bypass. Consequently later occurring complications can be eliminated by removing the implant.

Moreover a considerable reduction of weight is possible, because the food does no longer pass the stomach and the duodenum, gastric juices from the gallbladder and the pancreas can get into contact with the food later only and moreover the upper small intestine area is bypassed. Thus the active intestine surface is greatly reduced and nutrient absorption is massively reduced.

It is another advantage with respect to the gastric bypass that there is no need to delimit a stomach bag by clip suture instruments. Consequently no sutures which might entail later complications occur by the implant in this place.

The invention can be modified as it is shown in FIG. 3:

The flexible hollow body 1 can comprise an additional aperture 11 directed to the stomach. This aperture 11 is adjustable in its size and allows a natural passage for the food into the stomach. Thereby, the stomach is advantageously bypassed, for instance, for 90%, while 10% of the food comes into contact with the remaining stomach and the duodenum.

Furthermore it is possible to observe the remaining stomach through the aperture 11, for instance, via an endoscope after surgery, which has been impossible in conventional and laparoscopic methods yet.

The aperture 11 can include means (not shown) for changing its size, such as a lace for contracting the aperture 11.

The invention is not restricted by the above embodiments. Rather, the invention can be further modified within the scope of the present invention as defined in the claims.

I claim:

1. An implantable synthetic stomach for implanting inside the stomach of a patient comprising:
    a storage forming an antrum for storing food therein, said storage has an up-stream and a down-stream opening, a first tube connected to the storage at its up-stream opening, said first tube being insertable in a sealed manner into the esophagus of the patient and a second tube connected to the storage at its down-stream opening, said second tube being connectable in a sealed manner to a small intestine loop within the patient, wherein said storage is bulging relative to the first and second tube; and
    wherein said storage is designed as a rigid receptacle having more rigidity than the first tube and the second tube.

2. An implantable synthetic stomach according to claim 1, further comprising fixing means provided at free ends of said first and second tube, respectively for fixing the tubes to the respective parts of organs of the patient.

3. An implantable synthetic stomach according to claim 1, wherein said storage comprises an additional aperture forming an outlet into the stomach of the patient.

4. An implantable synthetic stomach according to claim 3, wherein said aperture includes means for changing its size.

5. An implantable synthetic stomach according to claim 1, further comprising means for adjusting the size of an additional aperture of the storage leading into the stomach of the patient such that about 10% of the food entering the storage comes into contact with the stomach and the duodenum.

6. An implantable synthetic stomach according to claim 1, further comprising means for adjusting the volume of said storage.

* * * * *